United States Patent
Campbell et al.

(10) Patent No.: US 11,241,260 B2
(45) Date of Patent: *Feb. 8, 2022

(54) FASTENER RETENTION SYSTEM FOR SPINAL PLATES

(71) Applicant: Alphatec Spine, Inc., Carlsbad, CA (US)

(72) Inventors: Christopher M. Campbell, Temecula, CA (US); Tyler Holschlag, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 16/365,230

(22) Filed: Mar. 26, 2019

(65) Prior Publication Data

US 2019/0216512 A1 Jul. 18, 2019

Related U.S. Application Data

(63) Continuation of application No. 14/549,965, filed on Nov. 21, 2014, now Pat. No. 10,258,387, which is a continuation of application No. 13/042,074, filed on Mar. 7, 2011, now abandoned, which is a continuation-in-part of application No. 11/771,383, filed on Jun. 29, 2007, now Pat. No. 9,078,718.

(Continued)

(51) Int. Cl.
*A61B 17/70* (2006.01)
*A61B 17/80* (2006.01)
*A61F 2/30* (2006.01)
*A61B 17/68* (2006.01)

(52) U.S. Cl.
CPC ...... *A61B 17/7059* (2013.01); *A61B 17/8042* (2013.01); *A61B 17/8061* (2013.01); *A61B 17/68* (2013.01); *A61B 17/80* (2013.01); *A61B 17/8023* (2013.01); *A61B 17/8033* (2013.01); *A61F 2002/30505* (2013.01); *A61F 2002/30517* (2013.01)

(58) Field of Classification Search
CPC ..... A61B 17/68; A61B 17/70; A61B 17/7058; A61B 17/7059; A61B 17/80; A61B 17/8023; A61B 17/8033; A61B 17/8042; A61B 17/8061; A61B 17/808; A61F 2/2846; A61F 2002/30517; A61F 2002/30505; A61F 2002/30565; A61F 2002/30571
USPC ......... 606/60, 246, 279, 280, 286, 288, 289, 606/294, 295, 296, 900, 901, 902, 914, 606/915
See application file for complete search history.

(56) References Cited

U.S. PATENT DOCUMENTS 7,632,361 B2 * 12/2009 Johnson .................. C30B 29/52
148/402
10,258,387 B2 * 4/2019 Campbell .......... A61B 17/8061
(Continued)

*Primary Examiner* — Marcela I. Shirsat
(74) *Attorney, Agent, or Firm* — Robert Winn

(57) ABSTRACT

A fastener retention system for retaining fasteners within apertures of an orthopedic plate includes a first pocket disposed between two of the apertures in the plate, a blocking member disposed between the two apertures and including a second pocket that forms a cavity with the first pocket, and a spring that expands from a compressed configuration within the first pocket to a decompressed configuration within the cavity.

20 Claims, 5 Drawing Sheets

Related U.S. Application Data

(60) Provisional application No. 60/818,030, filed on Jun. 30, 2006, provisional application No. 60/818,029, filed on Jun. 30, 2006.

(56) References Cited

U.S. PATENT DOCUMENTS

| | | | |
|---|---|---|---|
| 2004/0133205 A1* | 7/2004 | Thramann | A61B 17/8042 606/294 |
| 2006/0247639 A1* | 11/2006 | Anderson | A61B 17/8042 606/281 |
| 2008/0234680 A1* | 9/2008 | Zaiser | A61B 17/8023 606/71 |

* cited by examiner

FASTENER RETENTION SYSTEM FOR SPINAL PLATES

CROSS-REFERENCE TO RELATED APPLICATIONS

The present application is a continuation of U.S. application Ser. No. 14/549,965, filed Nov. 21, 2014, which is a continuation of U.S. application Ser. No. 13/042,074, filed Mar. 7, 2011, which is a continuation-in-part of Ser. No. 11/771,383, filed Jun. 29, 2007, which claims the benefit of U.S. Provisional Application Ser. Nos. 60/818,029 and 60/818,030, both filed Jun. 30, 2006. The entire contents of each of these applications are incorporated herein by reference.

FIELD

The present disclosure generally relates to the field of spinal orthopedics, and more particularly to fastener retention systems for spinal plates.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

The spine is a flexible column formed of a plurality of bones called vertebrae. The vertebrae include a hollow cavity and essentially stack one upon the other, forming a strong column for support of the cranium and trunk of the body. The hollow core of the spine houses and protects the nerves of the spinal cord. The different vertebrae are connected to one another by means of articular processes and intervertebral, fibrocartilaginous bodies. The intervertebral bodies, also known as intervertebral disks, include a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and consequently irritated. The result may be chronic and/or debilitating neck and/or back pain due to these spinal disorders.

One procedure for treating spinal disorders involves using substantially rigid plates for fixation of two or more vertebrae in desired spatial relationships and orientations relative to each other. During the procedure, the spine can be approached anteriorly or posteriorly. In either case, holes are drilled and tapped in at least two of the vertebrae to receive screws or other fasteners that secure the plate. The holes are positioned with reference to apertures formed in the plate. Typically the plate is curved about its longitudinal axis to facilitate contiguous surface engagement of the plate with the vertebrae. With the plate maintained against the vertebrae, the fasteners are driven into the vertebrae through the apertures in the plate. As a result the plate maintains the attached vertebrae in a desired spacing and orientation with respect to each other.

Over time, some fasteners may gradually work loose from the vertebrae. Slight shock or vibration of the vertebrae, due to walking, climbing stairs or more vigorous activity by the patient following treatment increases this tendency, jeopardizing the integrity of fixation. Moreover, as the fasteners work loose, the outward protrusion of the heads over other components of the fasteners can be a source of discomfort and present the risk of trauma to adjacent and surrounding soft tissue. Some plates include a retention mechanism that prevents the screws from working loose after fixation.

Occasionally, the fasteners may not be inserted at a proper insertion angle during the fixation procedure. When the fastener is inserted at an improper angle, the retention mechanism may not be able to contact the fastener as the fastener backs away from the vertebra. The retention mechanism may increase the complexity of manufacturing and assembly. For example, the spinal plate may require features such as additional openings in the plate to assemble the retention mechanism. These openings may decrease the structural integrity of the plate. The retention mechanism may require various features that interact with springs or other compression members that bias the retention mechanism in one or more directions. Additional features such as stops that prevent the retention mechanism from moving too far relative to the plate or from over-compressing the springs may also complicate manufacture and assembly.

SUMMARY

A fastener retention system for retaining fasteners within apertures of an orthopedic plate includes a first pocket disposed between two of the apertures in the plate, a blocking member disposed between the two apertures and including a second pocket that forms a cavity with the first pocket and a spring that expands from a compressed configuration within the first pocket to a decompressed configuration within the cavity.

In other features, the spring includes a height that is less than or equal to a depth of the first pocket when in the compressed configuration. The spring includes a height that is greater than a depth of the first pocket when in the decompressed configuration. The spring includes a plurality of flexible resilient members coupled by a plurality of hubs. The spring includes a radius of curvature in the decompressed configuration. The spring includes a central hub that contacts a surface of the first pocket in the compressed configuration and a surface of the second pocket in the decompressed configuration. The spring is further configured to bias the blocking member to protrude into at least one of the two apertures.

In still other features, the first pocket is disposed in a channel extending between the two apertures in the plate and includes a first depth D1. The blocking member is disposed in the channel and the second pocket includes a second depth D2. The spring is configured to compress to a first height H1 that is less than or equal to D1 when a first force is applied to the spring and expand to a second height H2 that is greater than D1 and less than or equal to the combined depth of D1 and D2 when the first force is released. The spring is further configured to engage with a portion of the blocking member when the first force is released and compress from a first length L1 to a second length L2 when a second force is applied to the blocking member.

A system for bone fixation includes an orthopedic plate having apertures configured to receive fasteners and a first pocket formed in a channel between two of the apertures, a blocking member that slides in the channel and includes a second pocket wherein the first and second pockets form a cavity between the blocking member and the orthopedic plate, and a spring that expands from a compressed configuration, wherein a height of the spring is less than or equal to a depth of the first pocket to a decompressed configuration, wherein the height of the spring is greater than the depth of the first pocket.

In other features, a first portion of the spring is configured to engage a wall of the second pocket in the decompressed configuration. A second portion of the spring is configured to engage a wall of the first pocket in the decompressed configuration. The spring biases the blocking member towards a top surface of the orthopedic plate in the decompressed configuration. The spring biases the blocking member towards a rest position substantially equidistant from the two apertures in the decompressed configuration. The spring includes a radius of curvature in the decompressed configuration that is less than a radius of curvature in the compressed configuration.

A method includes the steps of inserting a spring into a first pocket in a channel of a plate, inserting a blocking member having a second pocket into the channel of the plate, positioning the blocking member to align the second pocket and the first pocket forming a cavity, and expanding the spring to fill the cavity.

In other features, the method further comprises the steps of inserting a first screw into a first aperture adjacent to the first pocket to secure the plate to a vertebra, positioning the blocking member towards a second aperture that is opposite the first aperture and adjacent to the first pocket using the first screw, wherein the spring compresses, and decompressing the spring to bias the blocking member to align the second pocket and the first pocket.

In still other features, the method further comprises the steps of inserting a second screw into the second aperture to secure the plate to the vertebra, positioning the blocking member towards the first aperture using the second screw, wherein the spring compresses, and decompressing the spring to bias the blocking member to align the second pocket and the first pocket.

DETAILED DESCRIPTION

Figure 1:
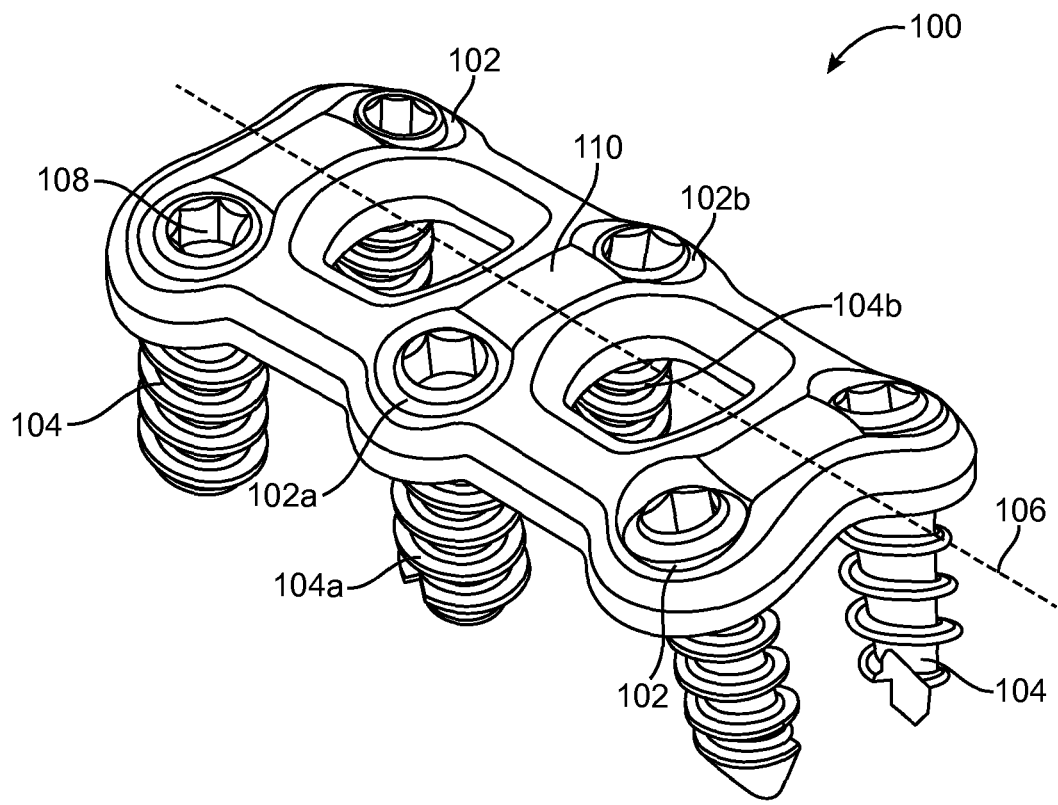
FIG. 1 is a perspective view of a spinal plate and a fastener retention system according to the principles of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Embodiments of the invention will now be described with reference to the Figures, wherein like numerals reflect like elements throughout. Embodiments of the invention may include several novel features, no single one of which is solely responsible for its desirable attributes or which is essential to practicing the invention described herein. The words proximal and distal are applied herein to denote specific ends of components of the instrument described herein. For example only, a proximal end refers to the end of an instrument nearer to an operator of the instrument when the instrument is being used. A distal end refers to the end of a component further from the operator and extending towards the surgical area of a patient and/or the implant. Similarly, the words left and right top and bottom, and upper and lower may denote opposite sides of a component.

Accordingly, a fastener retention mechanism for spinal plates of the present disclosure includes a blocking member and a spring that is compressible in multiple directions. The retention mechanism includes features that enable greater intrusion of the blocking member into the apertures to prevent fastener back-out from the vertebrae. The configuration of the spinal plate enables top-loading of the spring into a pocket of the spinal plate. The spring may be compressed in a first direction prior to insertion into the pocket of the plate. The blocking member may slide in place over the compressed spring. When the spring decompresses, the spring may fill the pocket and a cavity of the blocking member, thus enclosing the spring therebetween. The blocking member may slide towards a first one of two apertures to enable insertion of a fastener within a second one of the apertures. As the blocking member slides relative to the plate, the spring may compress in a second direction and bias the blocking member back to a rest position in which a portion of the blocking member intrudes upon the two apertures.

Referring now to FIG. 1, a spinal plate 100 includes apertures 102 that receive fasteners or bone screws 104 for attachment to two or more vertebrae (not shown.) The plate 100 may be, for example, a cervical plate that is configured for attachment to three cervical vertebrae. The plate 100 may be formed from a variety of materials such as physiologically inert metals, alloys, and/or plastics. For example, the plate 100 may be formed from a titanium and/or titanium-based alloy. The plate 100 is substantially symmetrical about a center line 106 that passes along a longitudinal axis of the plate 100. A surgeon may position the plate 100 over the vertebrae to be fixed and drill and tap holes in the vertebrae to receive the screws 104. In other examples, the screws 104 may be self-tapping. Each head 108 of the screws 104 includes a driving feature such as hexagonal or star configuration that enables the surgeon to begin to drive the screws 104 into the vertebrae. As the screws 104 advance further into the vertebrae, the heads 108 sink deeper into the apertures 102.

A retention mechanism 110, disposed between a first aperture 102a and a second aperture 102b, may be used to prevent a corresponding first screw 104a and a corresponding second screw 104b from backing away from the plate 100 should either become loose. As illustrated in FIG. 1, the apertures 102 may be formed in pairs along the center line 106. Each pair of the apertures 102 may include a corresponding retention mechanism. When the retention mechanism 110 is in a rest position or a locked position, as shown in FIG. 1, a portion of the retention mechanism 110 intrudes upon both apertures 102a and 102 b. Thus, if a screw should become loose and back away from the vertebra, the head 108 contacts the retention mechanism 110 preventing the screw from backing out any further from the vertebra.

Figure 2A:
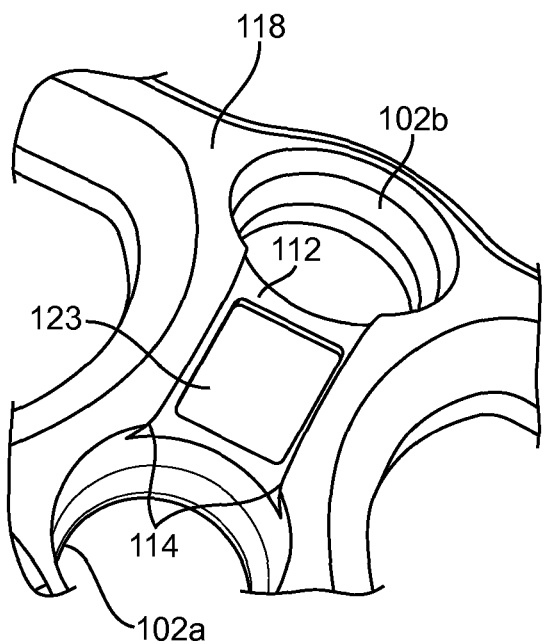
FIG. 2A is a partial perspective view of the spinal plate according to the principles of the present disclosure.
Figure 2B:
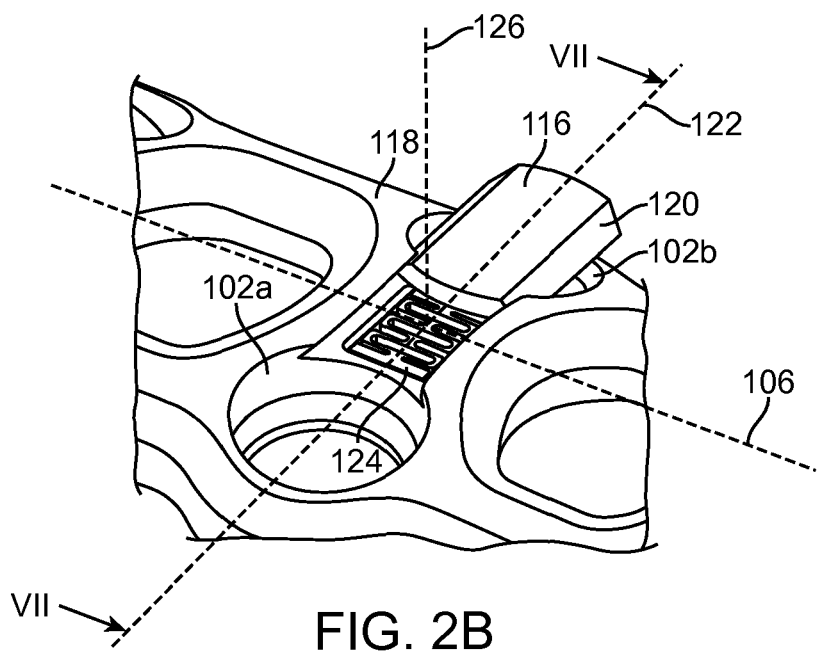
FIG. 2B is a partial perspective view illustrating assembly of the spinal plate and the fastener retention system according to the principles of the present disclosure.
Figure 2C:
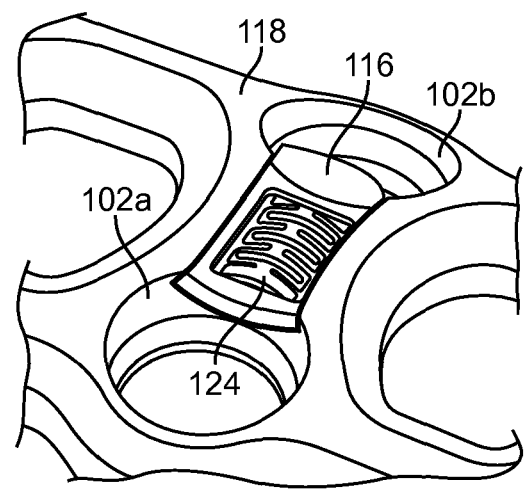
FIG. 2C is a partial perspective view of the spinal plate and the fastener retention system according to the principles of the present disclosure.

In FIG. 2A, a channel 112 formed in the plate 100 communicates with the first aperture 102a and the second aperture 102b. The channel 112 may run perpendicular to the center line 106. The channel 112 may include grooves 114 that are configured to slidably receive a blocking member 116 as shown in FIGS. 2B and 2C. For example, each of the grooves 114 may include a cantilevered projection or edge that extends from a top surface 118 of the plate 100 and over a portion of the channel 112. The blocking member 116 may include beveled edges 120 that form a substantially trapezoidal cross-section. The beveled edges 120 mate with the grooves 114 to prevent the blocking member 116 from exiting the channel 112 while allowing the blocking member 116 to slide substantially parallel to a lateral line 122 that is substantially perpendicular to the centerline 106.

Continuing with FIG. 2A, a pocket 123 may be formed in the channel 112. The pocket 123 may include a depression in the channel 112. The pocket 123 may include a length and width that form substantially a rectangular shape and include a depth D1 that is substantially less than an overall thickness of the plate 100, as shown in FIG. 6B. Referring now to FIGS. 2B and 2C, the retention mechanism includes a spring 124 that may be configured to rest within the pocket 123. The spring 124 may be compressible in multiple directions. For example, the spring 124 may include elements similar to an accordion spring that enable compression in a first direction along the lateral line 122 when a first force F1 is applied as shown in FIG. 4B. The spring 124 may also include elements similar to a leaf spring that enable compression in a second direction along a perpendicular line 126 that is perpendicular to both the center line 106 and the lateral line 122 when a force F2 is applied as shown in FIG. 6B.

The spring 124 may be formed from a variety of materials such as physiologically inert metals, alloys, and/or plastics. In other examples, the spring 124 may be formed from other materials that may not be physiologically inert because the spring 124 may be segregated from bone and/or tissue by the pocket 122 and the blocking member 116 as described below with reference to FIGS. 7A-7C.

Figure 3:
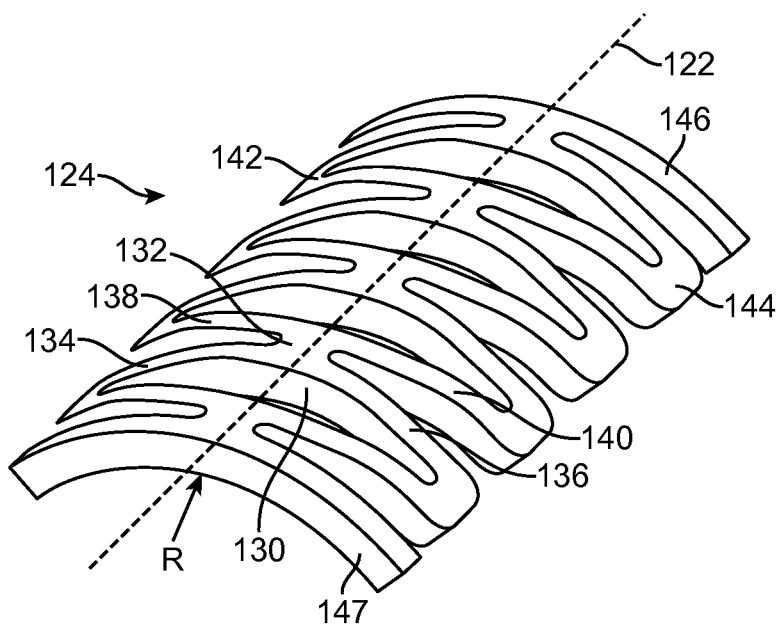
FIG. 3 is a perspective view of a spring of the fastener retention system according to the principles of the present disclosure.
Figure 4A:
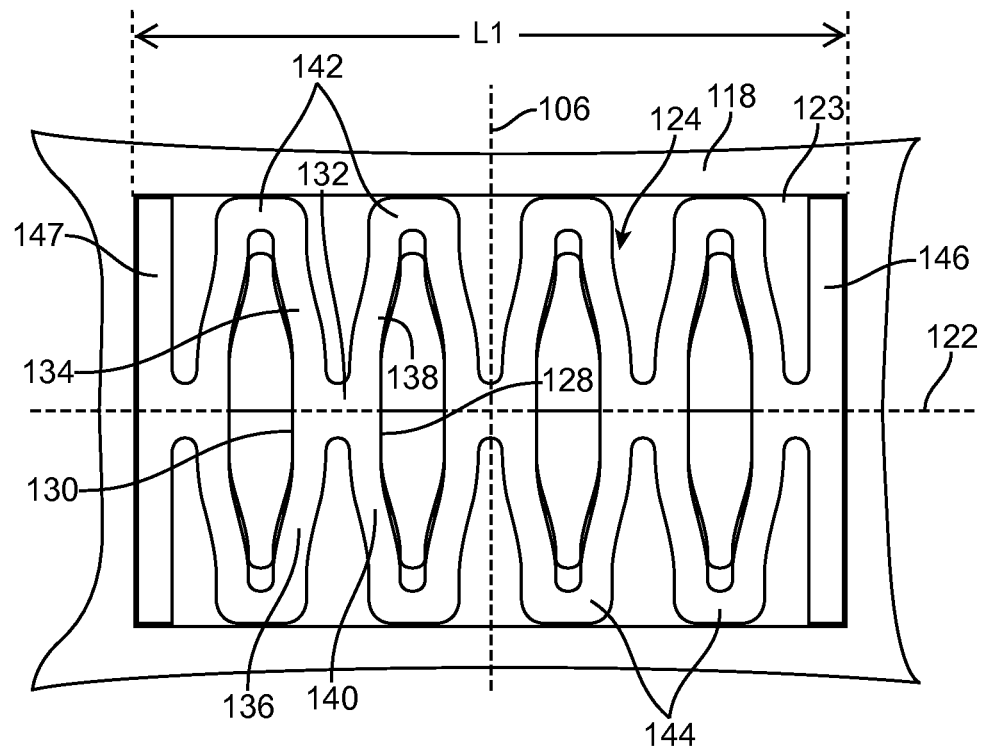
FIG. 4A is an elevational top view of the spring in a first decompressed position according to the principles of the present disclosure.
Figure 4B:
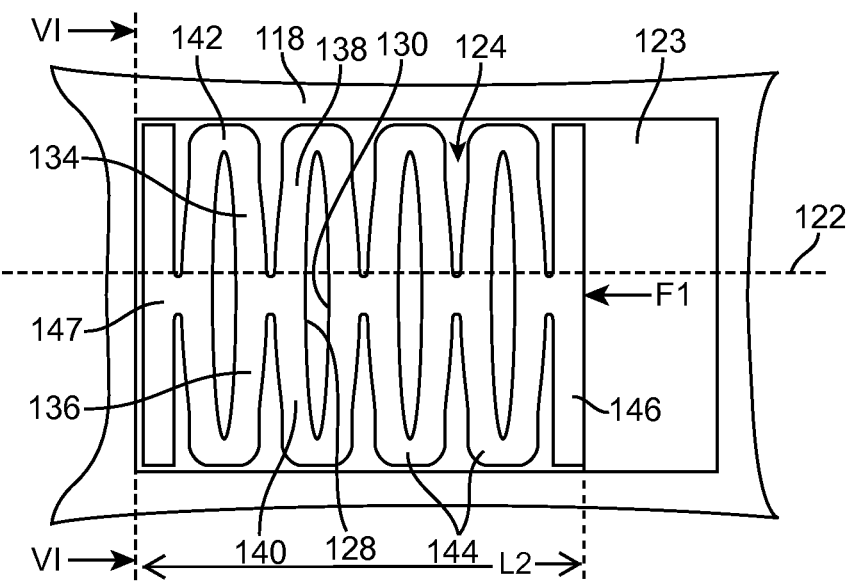
FIG. 4B is an elevational top view of the spring in a first compressed position according to the principles of the present disclosure.
Figure 5:
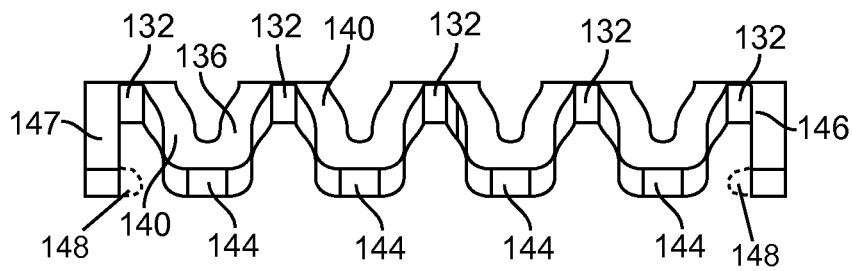
FIG. 5 is an elevational side view of the spring according to the principles of the present disclosure

Continuing now with FIGS. 3-5, the spring 124 may include various features that enable compression in the first direction that is substantially parallel to the lateral line 122. For example, the shape of the spring 124 may be substantially symmetrical about the lateral line 122 and perpendicular to the lateral line 122 along a right surface 128 and a left surface 130 of a central hub 132. A left upper rib 134, a left lower rib 136, a right upper rib 138, and a right lower rib 140 extend from each central hub 132 in a symmetrical fashion about lateral line 120. The ribs may be configured in a substantially linear fashion. Alternatively, the ribs may include some bends and/or some curvature. From left to right as depicted in FIG. 4A, each upper right rib 138 is coupled with each adjacent upper left rib 134 to form an upper hub 142, and each lower right rib 140 is coupled with each adjacent lower left rib 136 to form a lower hub 144. The leftmost and rightmost upper and lower ribs may not couple with adjacent ribs and instead may form end caps 146 and 147 of the spring 124.

Thus, each central hub 132 with a set of ribs 134, 136, 138, 140 may substantially form a resilient member that couples with an adjacent resilient member at the upper and lower hubs 142 and 144. For example, each resilient member may resemble an X-shaped member. In other examples, various suitably-shaped resilient members may be used to form various springs. For example, the spring may comprise substantially elliptically-shaped resilient members. The spring 124 may also comprise non-symmetrically-shaped resilient members. That is, the spring may comprise S-shaped resilient members, diagonal resilient members, and the like. In an uncompressed or decompressed configuration, such as when the spring 124 biases the blocking member 116 to the rest position, the spring 124 includes a length L1 that substantially fills the pocket 123 as shown in FIG. 4A.

Referring now to FIG. 4B, as the force F1 is applied on the end cap 146, the spring 124 will deflect in a linear and consistent manner until it cannot bend any further, at a point where the entire right surface 128 of one central hub 132 may be in contact with the entire left surface 130 of the next adjacent central hub 132. In this compressed configuration, the spring 124 includes a length L2 that is less than L1. The stiffness of the spring 124 may vary greatly as a function of the width, depth, thickness, material composition, and number of ribs and hubs within the spring 124. Thus, the spring 124 is compressible in a first direction that is substantially parallel to the lateral line 122. Furthermore, the spring 124 is self-limiting as the right surface 128 and left surface 130 contact one another thus preventing further compression due to the force F1. The spring 124 may include other self-limiting features, such as projections 148 on bottom portions of the end caps 146 and 147. The projections 148 may contact the upper and lower hubs 142 and 144 when the spring 124 is in the compressed configuration.

Figure 6A:
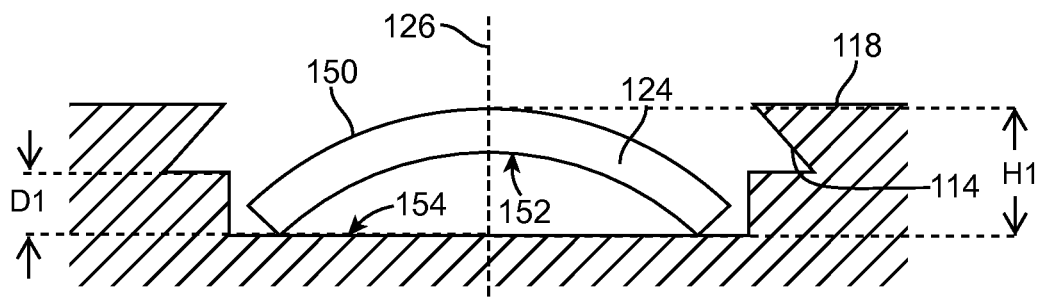
FIG. 6A is an elevational side view of the spring in a second decompressed position according to the principles of the present disclosure.
Figure 6B:
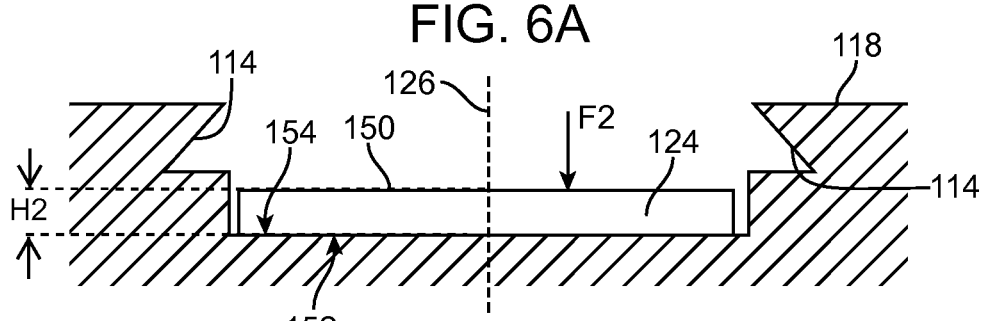
FIG. 6B is an elevational side view of the spring in a second compressed position according to the principles of the present disclosure.

Referring now to FIGS. 6A-6B, the shape of the spring 124 may include various features that enable compression in the second direction that is substantially parallel to the perpendicular line 126. For example, the spring 124 may include curvature of radius R applied to each resilient member. That is, the entire spring 124 from end cap 146 to end cap 147 may include curvature of radius R similar to a leaf spring as shown in FIG. 3. In other examples, each resilient member may include one or more curves or bends that substantially form a curved or angled profile. The curves or bends may be formed in a plane that is substantially parallel to a plane formed by the perpendicular line 126 and the center line 122.

Referring now to FIG. 6B, as a force F2 is applied to a top surface 150 of the spring 124, the spring 124 will deflect in a linear and consistent manner until it cannot bend any further, at a point where a bottom surface 152 of the spring 124 is substantially parallel to and/or contacts a base surface 154 of the pocket 123. In an uncompressed or decompressed configuration, the spring 124 may include a height H1. As the force F2 is applied, the spring 124 may be compressed to a height H2 that is less than H1.

Figure 7A:
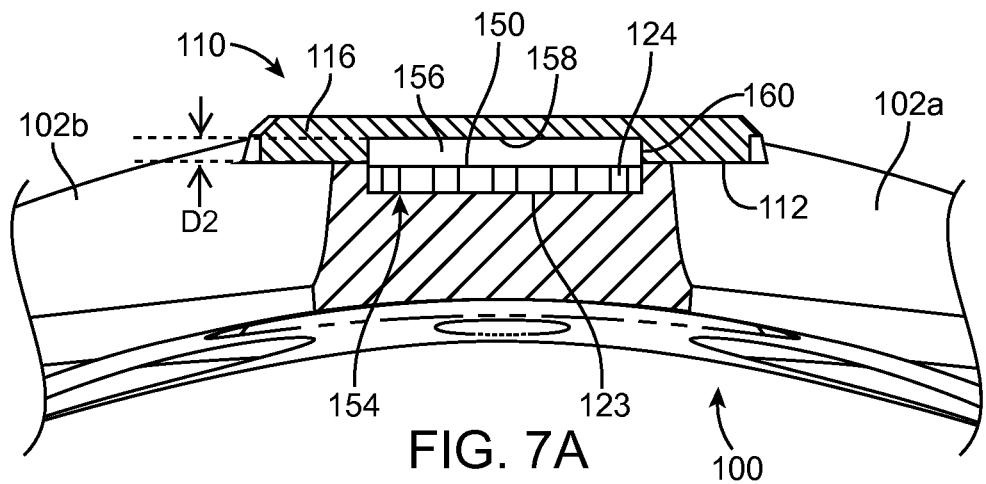
FIG. 7A is a cross-sectional view of the spinal plate and the fastener retention system illustrating the spring in the second compressed position according to the principles of the present disclosure.
Figure 7B:
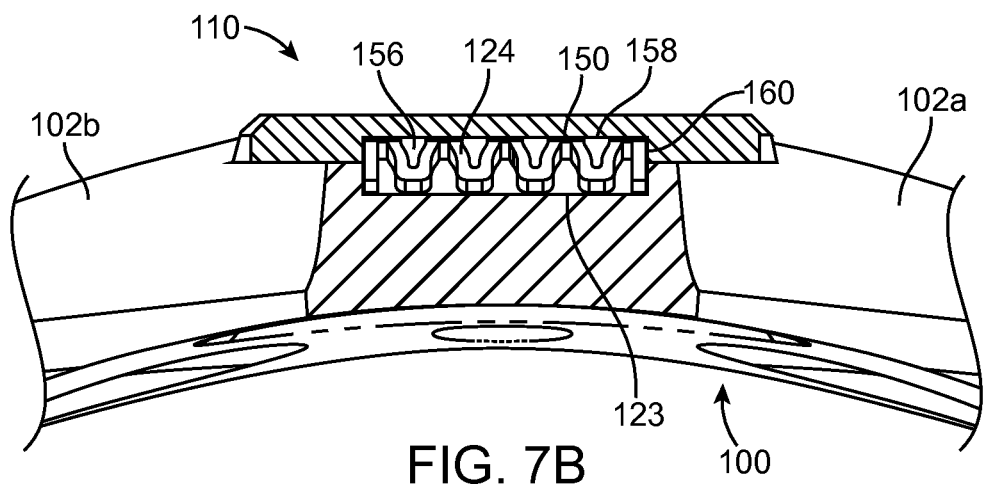
FIG. 7B is a cross-sectional view of the spinal plate and the fastener retention system illustrating the spring in the first and second decompressed positions according to the principles of the present disclosure.
Figure 7C:
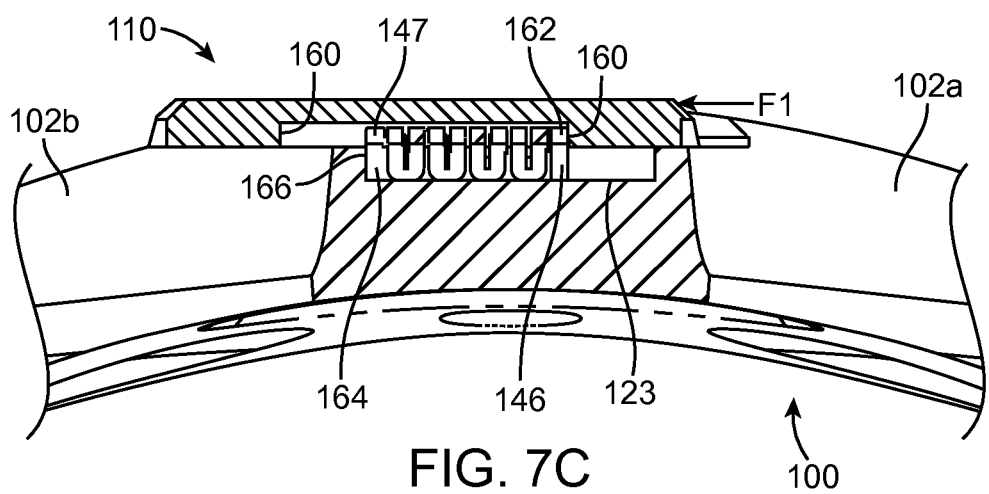
FIG. 7C is a cross-sectional view of the spinal plate and fastener retention system illustrating the spring in the first compressed position according to the principles of the present disclosure.

Referring now to FIGS. 7A-7C, partial cross-sectional views of the plate 100 and retention mechanism 110 illustrate interaction of the spring 124 with the plate 100 and the blocking member 116. In FIG. 7A, the spring 124 may be compressed to the height H2 so that the blocking member 116 may slide into place in the channel 112. For example, the force F2 may be applied to compress the spring 124 until the bottom surface 152 of the spring 124 is substantially parallel to or in contact with the base surface 154 of the pocket 123 as illustrated in FIG. 6B. That is, the spring 124 may be compressed until the height H2 is less than or equal to the depth D1 of the pocket 123. Once the blocking member 116 is centered over the pocket 123, a cavity 156 may be formed by a second pocket 158 in the blocking member 116 and the first pocket 123 of the plate 100. The second pocket 158 may include a depth D2.

Referring now to FIG. 7B, as the force F2 decreases, the spring 124 expands to fill the cavity 156 until the top surface 150 of the spring contacts the pocket 158 of the blocking member 116. That is, the spring 124 may decompress until the height H2 is greater than the depth D1 and less than the combined depth D1 and depth D2. In another example, the spring 124 may include material properties that enable the spring 124 to be flattened prior to loading within the pocket 123. For example, the spring 124 may include the radius of curvature R at one temperature and be flattened by increasing or decreasing the temperature of the spring 124 to a second temperature. That is, the spring 124 may comprise materials such as nickel titanium, commonly referred to as nitinol, that include shape memory and super elastic properties based on the temperature of the materials. Once the spring 124 has been flattened and loaded within the pocket 122, the blocking member 116 may be slid into place above the pocket 123 as described with reference to FIG. 7A. The temperature of the spring 124 may then be increased or decreased as necessary to regain the curved shape such that the spring 124 fills the cavity 156.

In FIG. 7C, the retention mechanism 110 moves to the first open position when the force F1 is applied, for example, by the head 108 of the first screw 104a being inserted into the first aperture 102a (not shown). An engagement portion 160 of the blocking member 116 engages a top portion 162 of the end cap 146 of the spring 124. A bottom portion 164 of the end cap 147 engages a side wall 166 of the pocket 122. Thus, as the force F1 is applied, the spring 124 begins to compress in the second direction from length L1 to length L2. Similarly, the force F1 may be applied in the opposite direction, for example, by the head 108 of the second screw 104b being inserted into the second aperture 102b (not shown). The retention mechanism 110 moves to a second open position. As the force F1 decreases, the spring 124 biases the blocking member 116 towards the rest or locked position and the length of the spring 124 returns to length L1.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents. The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

The invention claimed is:

1. An apparatus for fixation of two or more vertebrae, the apparatus comprising:
a plate configured to span at least from a first vertebra to a second vertebra, the plate having a depth extending from a top surface of the plate to a bottom surface of the plate;
first and second openings in the plate extending from the top surface to the bottom surface, the first and second openings configured to receive first and second bone screws, respectively;
a first pocket located on the top surface of the plate, the first pocket having a first length and positioned between the first and second openings, and the first pocket having a depth less than the depth of the plate;
a blocking member having a length sufficient to extend into both the first and second openings when the blocking member is centered between the two, the blocking member having a depth extending from a top surface of the blocking member to a bottom surface of the blocking member, the blocking member positioned over the first pocket, the bottom surface of the blocking member including a second pocket having a second length equal to the first length, and the second pocket having a depth that is less than the depth of the blocking member; and
a spring located in the first and second pockets;
wherein the spring operates to re-center the blocking member that is offset when a head of the first or second bone screw is advanced into the first or second opening; and
wherein the top surface of the blocking member does not include any openings.

2. The apparatus of claim 1, wherein the first pocket is located in a channel extending between the first and second openings.

3. The apparatus of claim 1, wherein the spring is configured to expand from a flattened configuration during assembly of the apparatus to a curved configuration.

4. The apparatus of claim 3, wherein the flattened configuration is achieved when the spring is exposed to a temperature at or below a first temperature and the curved configuration is achieved when the spring is exposed to a temperature at or above a second temperature, the second temperature being greater than the first temperature.

5. The apparatus of claim 3, wherein the spring in the curved configuration operates to re-center the blocking member.

6. The apparatus of claim 3, wherein the spring comprises a shape-memory alloy.

7. The apparatus of claim 6, wherein the spring comprises Nitinol or a nickel titanium alloy.

8. The apparatus of claim 3, wherein the spring comprises a super elastic alloy.

9. The apparatus of claim 8, wherein the spring comprises Nitinol or a nickel titanium alloy.

10. The apparatus of claim 3, wherein the spring when in the flattened configuration has a depth that is less than the combined depth of the first and second pockets.

11. The apparatus of claim 10, wherein the spring when in the curved configuration has a depth that is greater than the depth of the first pocket.

12. The apparatus of claim 3, wherein the spring in the curved configuration has a length equal to the first length of the first pocket.

13. The apparatus of claim 1, wherein the spring has a length equal to the first length of the first pocket.

14. An apparatus for fixation of two or more vertebrae, the apparatus comprising:
 a plate configured to span at least from a first vertebra to a second vertebra, the plate having a depth extending from a top surface of the plate to a bottom surface of the plate;
 first and second openings in the plate extending from the top surface to the bottom surface, the first and second openings configured to receive first and second bone screws, respectively;
 a first pocket located on the top surface of the plate, the first pocket having a first length and positioned between the first and second openings, and the first pocket having a depth less than the depth of the plate;
 a blocking member having a length sufficient to extend into both the first and second openings when the blocking member is centered between the two, the blocking member having a depth extending from a top surface of the blocking member to a bottom surface of the blocking member, the blocking member positioned over the first pocket, the bottom surface of the blocking member including a second pocket having a second length equal to the first length, the second pocket having a depth that is less than the depth of the blocking member, and the second pocket being accessible only from the bottom surface of the blocking member; and
 a spring located in the first and second pockets;
 wherein the spring operates to re-center the blocking member that is offset when a head of the first or second bone screw is advanced into the first or second opening.

15. The apparatus of claim 14, wherein the spring is configured to expand from a flattened configuration during assembly of the apparatus to a curved configuration.

16. The apparatus of claim 15, wherein the flattened configuration is achieved when the spring is exposed to a temperature at or below a first temperature and the curved configuration is achieved when the spring is exposed to a temperature at or above a second temperature, the second temperature being greater than the first temperature.

17. The apparatus of claim 15, wherein the spring in the curved configuration operates to re-center the blocking member.

18. The apparatus of claim 15, wherein the spring comprises a shape-memory alloy.

19. The apparatus of claim 18, wherein the spring comprises Nitinol or a nickel titanium alloy.

20. The apparatus of claim 15, wherein the spring comprises a super elastic alloy.

* * * * *